United States Patent [19]
Rodriguez

[11] 3,967,901
[45] July 6, 1976

[54] NEPHELOMETER HAVING MEANS SEMIAUTOMATICALLY CANCELLING COMPONENTS FROM SCATTERING BY PARTICLES SMALLER OR LARGER THAN THOSE OF INTEREST

[75] Inventor: Rodolfo R. Rodriguez, Columbia, Md.

[73] Assignee: Baxter Laboratories, Inc., Deerfield, Ill.

[22] Filed: July 31, 1975

[21] Appl. No.: 600,593

Related U.S. Application Data

[63] Continuation-in-part of Ser. No. 545,069, Jan. 29, 1975, abandoned.

[52] U.S. Cl. .............................. 356/103; 250/574; 356/36; 356/208
[51] Int. Cl.$^2$ ........................................ G01N 21/00
[58] Field of Search ............ 356/36, 102, 103, 208; 250/574; 328/165; 307/235 K

[56] References Cited
UNITED STATES PATENTS

3,758,787  9/1973  Sigrist ............................ 356/208 X

*Primary Examiner*—John K. Corbin
*Assistant Examiner*—Matthew W. Koren
*Attorney, Agent, or Firm*—H. Karl Saalbach; Herman L. Gordon; Richard G. Kinney

[57] ABSTRACT

An improved nephelometer for immunochemical complex assay measures forward light scatter in samples. The angle of forward scatter, about 30°, is small enough to result in a large amount of forward scatter from the immunochemical complex particles which are to be assayed, whose size is of the order of the wave length of the light used in the optical system. Forward scattering from smaller particles, such as from molecules of buffer, antibody and serum, is constant during the course of a test, and is compensated for by the use of subtraction circuits which are readily and semiautomatically adjusted to subtract proper values, in accordance with the readings taken on standard or "blank" samples of buffer, antibody and serum. Forward scattering from large particles, such as dust, is variable, and results in fluctuating signals, which are electrically processed to ignore the spurious peaks. The results of a test are displayed on a digital read out meter.

Also described is a method of and protocol for immunochemical assay, whereby the amount of antigen originally present in a sample is determined by adding a known amount of antibody, and by assaying the "blank" component ingredients and the resulting mixture.

5 Claims, 10 Drawing Figures

NEPHELOMETER HAVING MEANS
SEMIAUTOMATICALLY CANCELLING
COMPONENTS FROM SCATTERING BY
PARTICLES SMALLER OR LARGER THAN THOSE
OF INTEREST

CROSS REFERENCE TO RELATED
APPLICATIONS

This application is a continuation-in-part of a prior application and the benefit of the prior filing dates is claimed for any common subject matter. The application is:

Ser. No. 545,069, Filed Jan. 29, 1975 and now abandoned
For: METHOD AND APPARATUS FOR DISCRIMINATING AGAINST ARTIFACTS IN OPTICAL TESTING
By: Rodolfo R. Rodriguez This application is also related to a companion application:

Ser. No. 600,787 Filed July 31, 1975
For: NEPHELOMETER HAVING MEANS SEMI-AUTOMATICALLy CANCELLING COMPONENTS FROM SCATTERING BY PARTICLES SMALLER OR LARGER THAN THOSE OF INTEREST
By: Eugene K. Achter, Jerome C. Kremen, Rodolfo R. Rodriguez and Paolo Priarone

BRIEF SUMMARY OF INVENTION

This invention relates to the use of nephelometry to assay the amount of immuno-chemical complex present in a sample.

The invention is based on the fact that in an immunochemical complex assay, the various ingredients present have diverse sizes. The particles, including dissolved macromolecules, in buffer, antibody and serum are much smaller than the particles of immunochemical complex, while fortuitous particles of dust are generally much larger. As a result of this difference in size and the difference between the large concentration of buffer, antibody and serum present and the small concentration of dust present, it follows that the scatter due to the dust particles fluctuates while the scatter due to all other components is reasonably steady.

The nephelometer itself is characterized by these features:

The optical system uses an arrangement which accepts samples in test tubes and accurately measures forward scatter of a small volume of liquid, spaced within the walls of the test tube. The design of the optical system is such that specular reflection of the incident beam on the test tube walls does not interfere with measurement of the scatter, and thus commercial test tubes are satisfactory for use as test cells.

The angle of forward scatter is chosen to be about 30° from the illuminating beam within said small volume, as it has been found that for a broad range of angles centered on this value, the ratio of desired scattering, from the immunochemical complex particles of interest to the scattering, not of interest, by the larger and smaller particles that are present in the assay, is considerably higher than at other scattering angles.

The scatter due to large particles, such as dust, is irregular and is ignored by the electronic circuitry, which measures the minimum value of scatter signal over a period of time.

The value of scatter due to particles smaller than those of interest is subtracted from the total scatter to determine the amount of scatter from particles of interest. This subtraction is done semiautomatically by the instrument, in accordance with readings made on the standard or "blank" solutions of the particles smaller than those of interest.

There is described below a certain protocol in accordance with which the assay is performed.

BRIEF DESCRIPTION OF VIEWS OF DRAWING

BACKGROUND OF INVENTION

Figure 1:
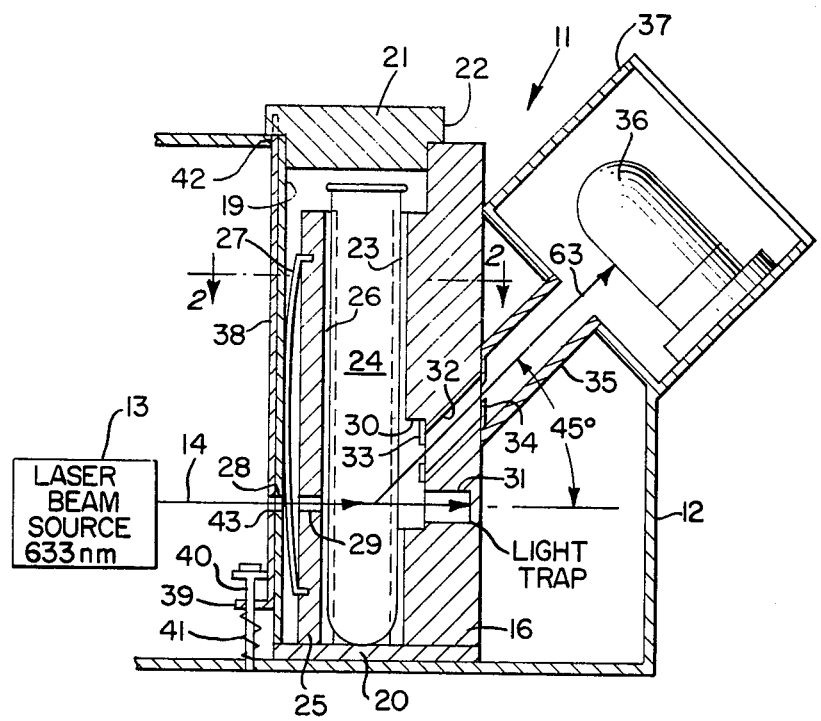
FIG. 1 is a vertical cross-sectional view taken through the optical portion of an improved immunoassay nephelometer constructed in accordance with the present invention.

In the biological laboratory nephelometry is a standard tool for quantitatively measuring the amount of certain biologicals in a liquid sample. The measurement is made by directing a beam of light through the liquid, and determining the amount of liquid which is scattered at different angles. The amount which is scattered depends on the size of the scattering particles, their concentration, their shape, the wavelength of the light used, the refraction indexes of the particles and of the medium in which they are suspended, and the angle at which the scatter is measured. There is a vast body of learning which enables a determination of the concentration to be made from such observations, if the distribution of particle sizes is known, but there are practical difficulties.

For example, in the particular instance which led to the present invention, it was desired to measure the amount of an immunochemical complex in a sample.

From filtration tests made to determine the approximate size of the particles giving rise to the desired and undesired scattering signals, respectively, it was determined that the desired immunochemical complex will pass through a 0.4 micron filter but is stopped by a 0.2 micron filter. Its size is therefore, roughly, about 300 nanometers.

The angle chosen for measurement of the scattered light strongly influences the magnitude of the measurement. A small forward angle increases the amount of scattered light, as is obvious when considering the appearance of lights at night through a fog. Furthermore, the larger and medium sized particles are relatively more effective in scattering light at small forward angles than are the small particles. Thus, in order to minimize the contribution of small sized particles, small forward angles are desirable. However, strong scattering is also obtained from large dust particles which are unavoidably present in the samples. Thus, to minimize the contribution of large sized particles, larger angles of forward scatter should be used.

In making the measurement, the invention seizes on the fact that the particles which are of interest are the largest of the particles present in a constant macroscopic manner. Larger particles, namely, dust, dance around in the solution and their scattering is not constant because the dust particles, relatively few in number from a statistical point of view, are not constant in the field of the light beam.

Accordingly, the invention measures the desired component by subtracting from the observed value the constant contribution from particles smaller than those of interest while electrically suppressing the fluctuating contribution from dust, so that it is not included in the measurement.

It has been found that there is a broad range of forward scatter angles, centered at about 30°, where the angle chosen increases the ratio of scatter by medium and large sized particles to scatter by small sized particles, without also increasing the scatter from the large sized particles to such an extent as to overload the ability of the electrical system to suppress the fluctuating component representing the large sized particles.

DETAILED DESCRIPTION

Referring to the drawings, 11 generally designates the optical portion of a nephelometer in accordance with the present invention. The nephelometer 11 comprises a housing 12 in which is suitably mounted a horizontally-directed laser unit 13, for example, a Model 155 laser unit, manufactured by Spectrophysics, Mountain View, California, which generates a 632.8 nm (nanometer) laser beam, shown at 14.

Housing 12 is provided with a vertical sample-receiving chamber 15 having a relatively thick right side wall 16, as viewed in FIG. 1, front and rear walls 17 and 18, a left side wall 19, and a bottom wall 20. Chamber 15 is provided with a removable top cover 21 having a peripheral flange 22.

Figure 2:
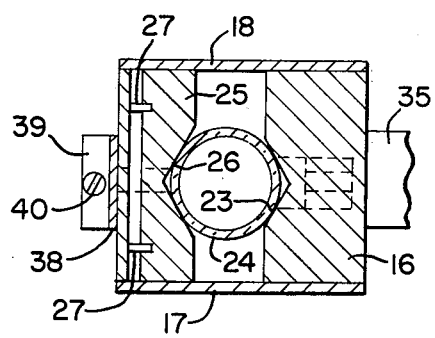
FIG. 2 is an enlarged horizontal cross-sectional view taken substantially on the line 2—2 of FIG. 1.

Right side wall 16 is formed with an inwardly facing vertical V-groove 23 adapted to be engaged by a conventional vertically positioned test tube 24. A vertical pressure block 25 formed with an inwardly facing vertical V-groove 26 is slidably positioned in the left side chamber 15, as viewed in FIG. 1, and is provided with a pair of vertical bowed wire springs 27, 27 secured symmetrically to the left side face of the block so as to bear against chamber wall 19 and cause the V-grooved block 25 to exert positioning spring force against the test tube 24 to hold the test tube firmly against V-groove 23 of wall 16, as shown in FIG. 2.

Wall 19 and block 25 are formed with respective laser beam apertures 28 and 29 aligned with beam 14. Wall 16 is formed with a vertically extending recess 30 including a light trap recess 31 aligned with beam 14 and lined with suitable light-absorbing material. Recess 30 communicates with a 45°-inclined light passage 32 formed in wall 16 and provided at its opposite ends with collimating field stops 33 and 34 having 2.8° divergence round field stops as above described, aligned at 45° with respect to beam 14 and aimed, for a conventional 12 × 75 mm test tube 24 at a point on the wall of the test tube about 3.07mm above the beam center line.

Field stop 34 opens into a light tube 35 leading to a photomultiplier tube 36 mounted in a chamber 37 provided therefor on housing 12, as shown in FIG. 1.

In some conventional nephelometers utilizing test tubes as test cells, the incident beam and the observed scatter lie in a plane perpendicular to the axis of the test tube. In such an arrangement, incident rays are multiply reflected from the sides of the test tube in the same plane as the observed scatter and are picked up without discrimination. One of the features of the instant nephelometer is the placement of the test tube axis in the same plane as that of the incident and scattered rays, thus avoiding the spurious signal due to multiple reflections from the sides of the test tube. These spurious signals are not reproduceable, using different test tubes. The multiple reflections referred to are those at the glass-air interface, and they exist in the absence of imperfections, but are widely different with different test tubes because of the large number of reflections involved.

Figure 4:
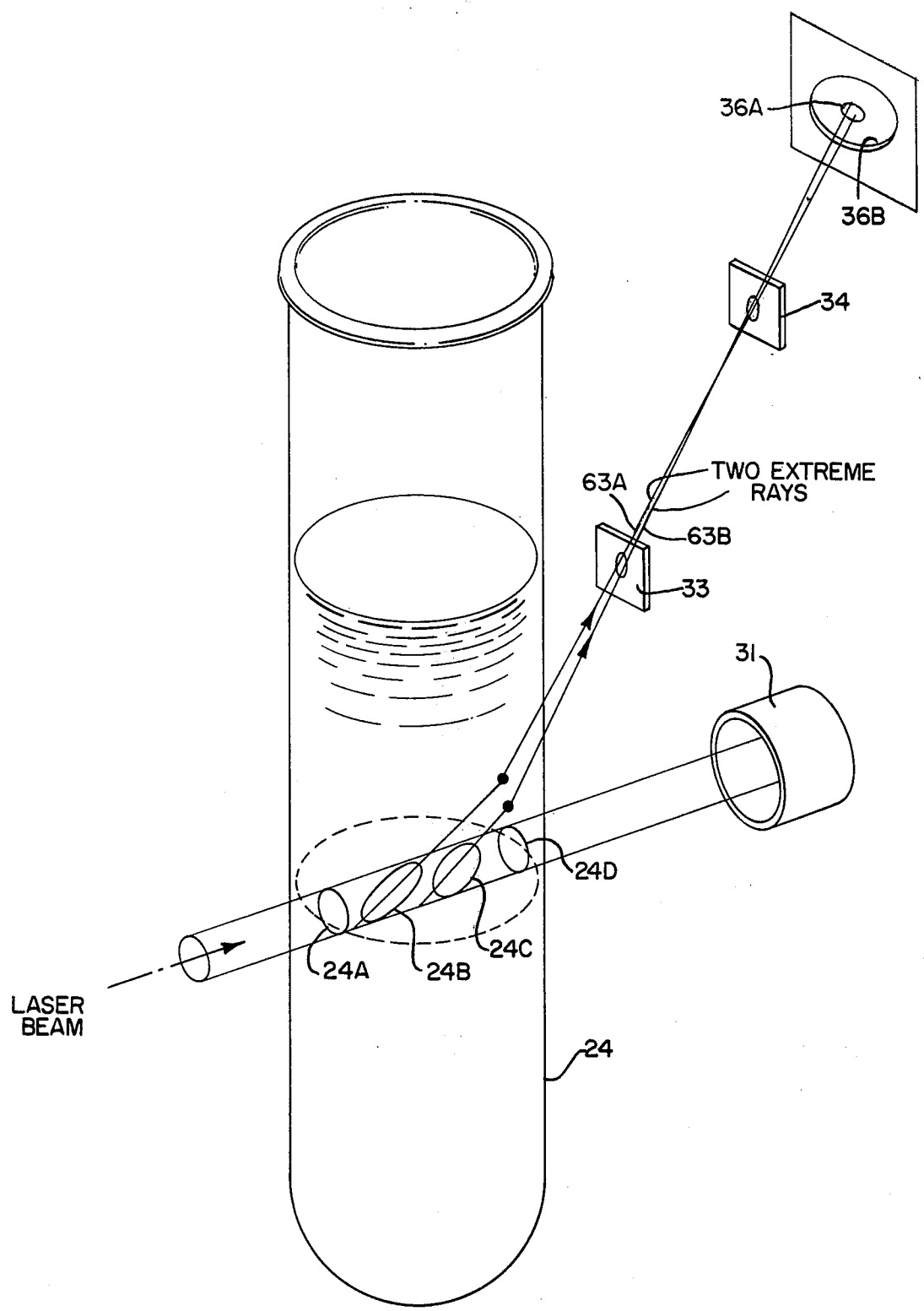
FIG. 4 is a perspective diagram, corresponding to FIG. 3, illustrating how the photomultiplier field of view is restricted by field stops so as to permit it to observe forward scatter from only a limited portion of the sample within the test tube.

As can be seen from FIG. 4, the laser beam strongly illuminates a section of the test tube 24 and its contents between entrance 24A and exit 24D. At these two spots, the unavoidable surface deposits and artifacts usually found on and in the glass or plastic of laboratory test tubes or cuvettes and the irregularities of the tube-liquid interface and tube-air interface cause a strong forward scatter, which is unrelated to the forward scatter which it is desired to measure. In order to eliminate this undesired forward scatter from the measurement, field stops 33 and 34 cooperate to define a family of extreme rays, two of which, 63A and 63B, are shown. These two extreme rays lie in a vertical plane containing the vertical diameter of each of the field stops 33 and 34. These two extreme rays, which are shown as breaking at the rear surface of the test tube, define a part of the front and rear limits of view 24B and 24C. The portion of the test tube volume between these two limits of view and also illuminated by the laser beam, is accessable to view by the photomultiplier tube 36. This tube has an entrance aperture 36B which is larger than, and surrounds the exit aperture 36A of the field stops 33 and 34.

The field stops 33 and 34 are mounted vertically and therefore define a field of view whose right cross section is elliptical rather than round. This is a matter of convenience in using round field stops and vertical mountings.

Although the effectively used portion of the tube 24 appears in FIG. 4 to extend almost from inner tube wall to inner tube wall, the showing is exaggerated to render details visible. In our preferred embodiments, we have used an effective portion about 1 millimeter in major dimension, near the center of a 10 millimeter diameter test tube. This disproportion in size increases the accuracy of measurement.

Designated at 38 (FIG. 2) is a safety shutter plate which is slidably engaged against left wall 19 and which has a bottom flange 39 through which is slidably received a headed vertical pin 40 rigidly secured to the bottom wall of housing 12. A coiled biasing spring 41 surrounds the lower portion of the pin 40 and bears between flange 39 and the housing bottom wall. The top end of plate 38 extends through a guide slot 42 in the top wall of housing 12 located beneath the peripheral flange 22 of top cover 21. Shutter plate 38 has a light aperture 43 which is moved into registration with wall aperture 28 when top cover 21 is seated in closed position over the top end of chamber 15, as shown in FIG. 1. When the cover 21 is removed, spring 41 elevates the shutter plate 38 into blanking position covering aperture 28. This insures against dangerous laser flash hazards which may be present when an operator looks downwardly into the test tube 24 with cover 21 removed.

Figure 3:
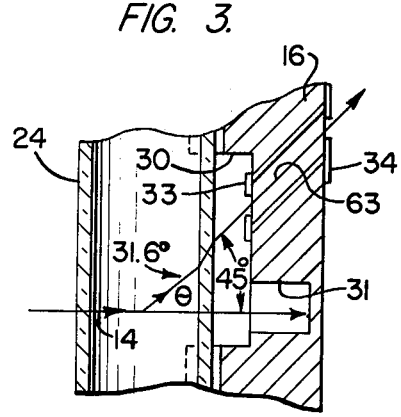
FIG. 3 is an enlarged fragmentary vertical cross-sectional view of the light-scattering portion of the nephelometer of FIG. 1.

As above explained, and as shown in FIGS. 3 and 4, there is refraction at the wall of test tube 24, so that the exit angle of the scatter beam, shown at 63, is 45° to the incident laser beam 14, whereas inside the test tube the scatter angle is 31.6° to the incident laser beam. The angle 45° is a convenient manufacturing angle, and the consequential angle of 31.6° has been found to give a high ratio of scattering from immuno-chemical complex particles to scattering from smaller particles, without overloading the electrical processing circuit (which will be explained below) with excessive fluctuating noise signals arrising from the presence of large particles, such as dust. It will also be seen that the angled scatter beam seen by the photomultiplier tube 36 is in a vertical plain containing the axis of the test tube, thereby eliminating artifacts due to internal reflections in the test tube, as above explained.

Test tubes satisfactory for use with the invention are from commercial stock. For example, ordinary Kimble test tubes, 10 × 75 mm, are satisfactory, unless they have defects in the wall obvious to brief visual inspection.

In operation, particles of approximately 0.3 micron size in the liquid in test tube 24 scatter the laser beam 14 strongly along the optical path defined by the field stops 33, 34 and generate corresponding signals in the photomultiplier tube 36, so that these signals can be used to measure the amount of antigen originally present in the test tube, after a known amount of antibody material is added to the liquid contained in the test tube.

Figure 5:
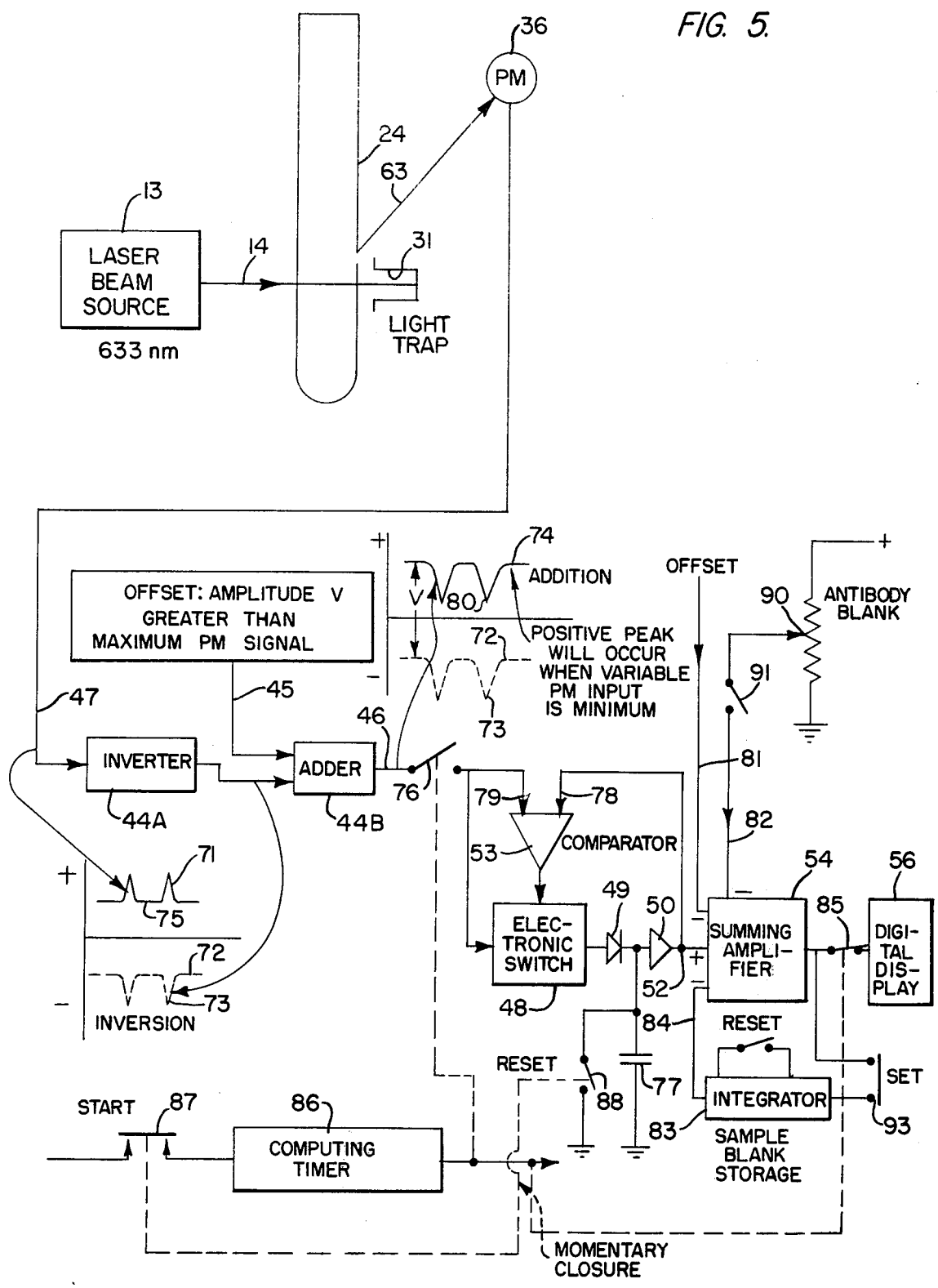
FIG. 5 is a simplified block diagram of the electrical signal processing and control circuitry of the nephelometer.

At low antigen levels and relatively low forward scattering angles, such as the angle employed herein (approximately 31.6°) the influence of dust particles in the test tube, and similar artifacts, becomes quite important and presents a source of serious error. The drawing, FIG. 5, illustrates in block form a signal-handling circuit which discriminates against sporadic positive spike effects caused by such dust particles or other artifacts. This circuit is a signal processing circuit which clips out positive peaks in the photomultiplier output signal, so that said positive peaks never get sent on to and processed by the measuring equipment. These positive peaks are generated by the dust particles in the liquid under examination, or the other abovementioned artifacts. Thus, because of dust particles, for example, the photometer signal generated in photomultiplier tube 36 is variable, with large positive spikes 71 caused by the individual dust particles. The variable photomultiplier signal is applied at 47 to one input of an inverter 44A and adder 44B. A steady offset voltage greater than the maximum photomultiplier signal is applied at 45 to the other input of inverter 44A and adder 44B. The input signal at 47 is inverted in the inverter 44A, as shown at 72, and the inverted peaks are shown at 73. The steady positive input voltage applied at 45 is added in the adder 44B to the signal 72, and the resultant positive output signal at 46, shown at 74, has positive maxima corresponding to the original minimum values 75 of the input signal applied at 47.

The output signal at 46 is passed through a timer switch element 76, an electronic switch 48, a diode 49 and an operational amplifier 50, providing an output signal at 52 in the form of a positive peak when the variable input at 47 is a minimum. The greatest positive peak signal during the sampling period reaching operational amplifier 50 is held in capacitor 77 to develop a steady comparison signal, available at 52, which is applied at 78 to one input of a comparator 53. The output signal 74 from device 44 is applied (with timed switch element 76 closed) to the other input 79 of comparator 53. Switch 48 will close initially at the initial value of curve 74. Capacitor 77 will charge to this value, at which point switch 48 will open by the action of comparator 53. The value at 52 will be held until the curve 74 amplitude exceeds the initial stored highest point value at 52, at which point switch 48 will again close. The value at 52 will now assymptotically track (increase) the relatively stable positive maximum values of curve 74, giving a new stored value at 52. Curve 74 will continue to establish such new stored values (with each increase). The comparator ignores the effects of minima caused by artifacts (such as minima 80). At any time that the amplitude of curve 74 goes below the tracked stored value at 52, switch 48 opens, and the signal at 46 is not forwarded to the integrating capacitor 77 for storage. Nor can the positive signal stored in capacitor 77 be lost unless reset switch 88 is closed. These positive signals cannot be lost through diode 49 when the signal at output 46 is more negative (as at 80) than the value stored in integrating capacitor 77 because of the poling of diode 49, which permits positive charge to flow only from left to right. The positive signals cannot be lost through operational amplifier 50 because the input impedance of the operational amplifier is enormous, amounting effectively to an open circuit.

Thus, electronic switch 48 opens when the signal at 78 is greater than the signal at 79. The maxima of signal 74 will, however, be stored in integrating capacitor 77. The stored signal at 52 is thus compared with the instantaneous signal at 46 in the comparator 53, whose output controls switch 48 so that switch 48 is held closed only when the variable input at 47 is higher than a previously stored value. Therefore, switch 48 is normally closed (no signal at 52) and opens when the signal 74 goes below its prior stored value.

The desired positive antigen scatter signal at 52 is summed in an algebraic summing amplifier 54 with a suitable negative offset signal applied at 81, with a negative antibody blank signal applied at 82, adjusted in a manner presently to be described, and with a negative stored serum (antigen) blank signal from an integrator 83, applied at 84. The output signal from amplifier 54 is delivered through a timed switch element 85 to a digital display device 56. The display provided by device 56 is for a selected period of operation of the algebraic summing amplifier 54, controlled by a manually activated computing timer 86. Timer 86 is designed to provide a signal sampling period of at least several seconds in order to discriminate adequately against large dust particles or similar artifacts.

When timer 86 is activated by its starting switch, shown at 87, it discharges the signal storage capacitor 77 by momentarily closing a reset switch 88 connected across the capacitor, closes the timer switch element 76 and opens the switch element 85. This provides several seconds for the accumulation of the antigen scatter signal in capacitor 77. At the end of the timed period, switch element 76 opens and switch element 85 closes, thereby transferring the summed voltages from the algebraic summing amplifier 54 to the digital display device 56, which produces a digital display indicative of the summed voltages.

The negative antibody blank adjustment signal at 82 is obtained from a potentiometer 90 connected to a suitable voltage source. The potentiometer is adjusted (with its control switch 91 closed) to provide a negative signal at 82 such as to give a zero readout on device 56 in a prior test on a blank reference sample of antibody material.

The negative antigen (serum) blank signal at 84 comprises a compensation signal obtained from the output of algebraic summing amplifier 54, with the antibody blank switch 91 open, in a prior test on a plain antigen reference sample before antibody material is added. This antigen (serum) blank signal is stored in integrator 83 by activating a "set" switch 93 during such a prior test. The stored negative antigen blank signal is then available to supply the required compensating negative blank antigen (serum) signal at 84 during the test on the final mixture above described.

It will therefore be seen that by subtracting the present antibody blank signal at 82 and the stored antigen blank signal at 84 from the main test signal at 52, the required discrimination against other particles, such as free antibody and other particles in the antibody blank and free antigen and other particles in the serum blank, is accomplished, and the digital display of the immunocomplex particles is not affected by the presence of said other particles in the final test mixture. This digital display can therefore be used to provide an accurate indication of the amount of antigen originally present in a sample after the sample has been exposed to a known quantity of antibody reagent.

Figure 6:
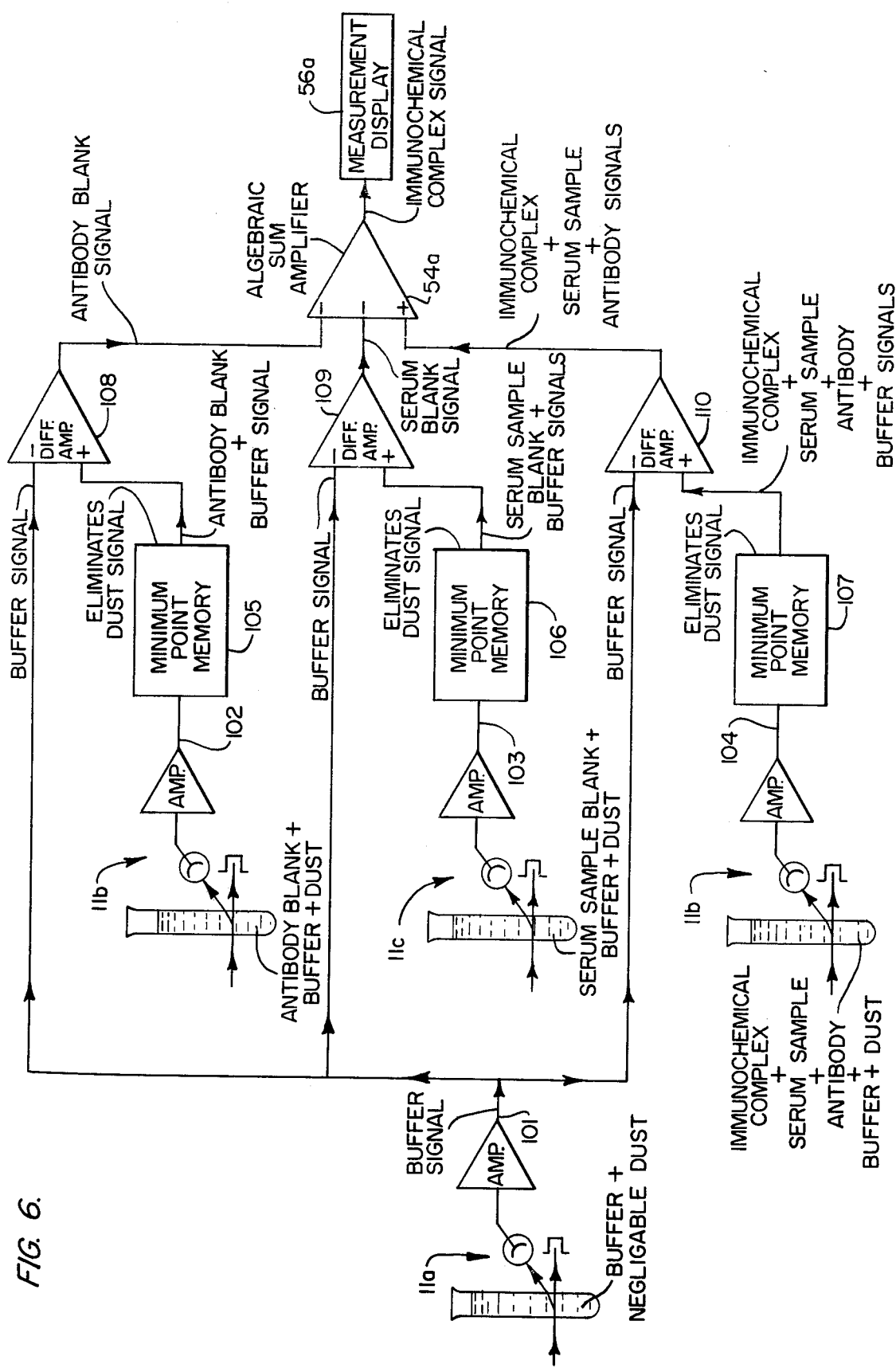
FIG. 6 is a block diagram of another embodiment of immunochemical complex nephelometry assay system.

The operation of the system of FIG. 5 can be understood more easily if it is compared to that of the simpler embodiment of FIG. 6. These two embodiments differ in that the system of FIG. 6 is a four-channel system in which four optical measurements are simultaneously made and simultaneously processed to produce the desired measurement display at 56a. In the system of FIG. 5 the corresponding four optical measurements are sequentially made, the results of the first three tests are stored, and these stored measurements are combined with the fourth measurement to give a measurement indication at digital display 56a.

In FIG. 6 there are four optical test stations 11a to 11d. At station 11a, a forward scatter measurement is made of the buffer solution, which is available in such purity as to contain negligible dust. Each of the other biological reagents which must be used, the antibody and the serum, which are measured at stations 11b and 11c, necessarily have dust in them because of the manner in which they are obtained. At the fourth station there is measured a solution which contains as ingredients both the antibody and the serum sample, which react to produce the immunochemical complex whose concentration is to be indicated at 56a.

The signal at line 101 is one which corresponds substantially only to the scattering property of the pure buffer. Since buffer is in the mixtures at stations 11b to 11d, and the buffer signal is similarly subtracted from other signals at difference amplifiers 108 to 110, the buffer signal, in effect, sets the zero operating point or datum reference for the instrument.

The signals at lines 102 to 104 are irregularly affected by dust, and the dust signals are eliminated by means of the minimum point memory circuits 105 to 107. These circuits correspond to the minimum point memory circuit of FIG. 5, comprising integrator capacitor 77, diode 49, electronic switch 48 and comparator 53.

The signals from differential amplifiers 108 to 110, when combined in proper sense in algebraic sum amplifier 54a, produce the immunochemical complex signal which is fed to measurement display 56a.

It will be seen, by tracing the signals in FIG. 6, that each of the undesired signals is eliminated from the output of algebraic sum amplifier 54a, either by cancellation in minimum point memories 105 to 107 or by subtraction in differential amplifiers 108 to 110 or algebraic sum amplifier 54a.

Figure 7:
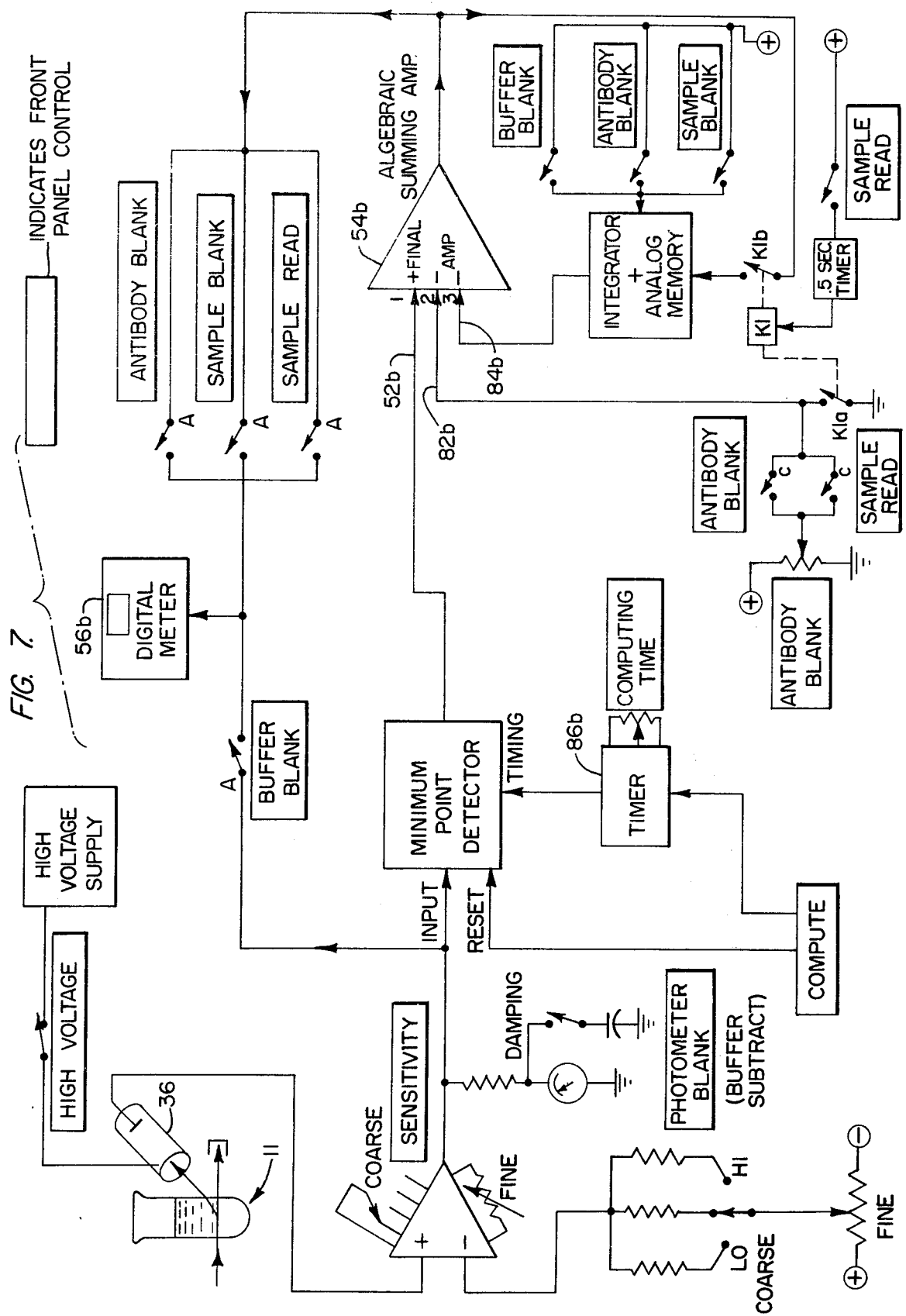
FIG. 7 is a diagram of the electrical control and measurement sections of the nephelometer, showing the relationship of the parts to the front panel controls.

FIG. 7 is a simplified block diagram of the invention showing how the objectives are accomplished. No attempt has been made to illustrate the actual circuits, but to show functional characteristics. Probably the best way to describe the operation of the system is to follow the protocol and explain what happens as the operator adjusts the knobs or pushes the different buttons. For this purpose the diagram shows, adjacent the appropriate place in the circuit, the label which is affixed to the front panel control which is manipulated by the operator during the test.

A significant point that must be remembered for proper understanding is that there are four SPECIMEN SWITCH positions, BUFFER BLANK, ANTIBODY BLANK, SAMPLE BLANK, and SAMPLE READ, which are mutually exclusive.

Protocol

A. After a 30 minute warm-up, turn HIGH VOLTAGE on. This connects negative voltage to the cathode of the photomultiplier tube.

B. Lift sample station cover. PHOTOMETER BLANK switch to MEDIUM. SENSITIVITY switch to X30. Adjust analog meter to zero using the PHOTOMETER BLANK fine controls. This step established electronic "zero".

C. Put a tube containing the highest "reference" concentration of antigen/antibody into the sample station and adjust the sensitivity controls until the analog meter reads 9 (or any other agreed upon value). Adjustment of sensitivity insures that all further readings will be in scale.

D. Set SPECIMEN SWITCH to BUFFER BLANK. The digital meter is connected to the output of the variable gain photometer. All other parts of the circuit are disconnected from the digital meter.

E. Insert buffer blank tube in optical station and adjust the value of the digital meter to zero using the PHOTOMETER BLANK subtract controls. For most immunology experiments the coarse PHOTOMETER BLANK switch will remain set at MEDIUM.

The error contributed by the buffer scatter will now be subtracted from all subsequent readings, taken on other tubes.

F. Adjust ANTIBODY BLANK potentiometer fully clockwise to the zero position. This ensures that in the next step the antibody blank subtract will be set at zero.

G. Set SPECIMEN SWITCH to ANTIBODY BLANK, resulting in these occurrences:
  i. The integrator is reset to zero and, therefore, input No. 3 to final amplifier is zero.
  ii. Input No. 2 to final amplifier is connected to ANTIBODY BLANK potentiometer which was set at zero.
  iii. Digital meter is now connected to output of final amplifier. Number displayed is the result of the previous operation, therefore, it is ignored.

H. Insert antibody blank tube in optical station and push COMPUTE. First, the minimum point memory is reset to zero; then, the minimum point detector will examine the output of the variable gain photometer for a pre-determined period set by the COMPUTING TIME control and at the end of that period store the lowest amplitude which has occurred. The digital meter displays that same value, since inputs 2 and 3 of final amplifier are zero.

I. Adjust ANTIBODY BLANK potentiometer CCW until the digital meter reads zero. Voltage at pin 2 of final amplifier is increased until it equals the value at the output of the minimum point detector. Since that value is the value of the antibody blank, the antibody blank value is permanently recorded in the potentiometer.

J. Set SPECIMEN switch to SAMPLE BLANK. The digital meter still reads the output of the final amplifier, the integrator is still set to zero and the ANTIBODY BLANK potentiometer is disabled. The number displayed is the value of the antibody blank obtained in previous steps.

K. Insert the sample blank tube into the optical station and push COMPUTE. The minimum point memory is reset to zero. The minimum point detector examines the output of the variable gain photometer and stores the minimum point. The number displayed in the digital meter is, therefore, the value of the serum blank.

L. SPECIMEN switch is set to SAMPLE READ. The digital meter still reads the output of the final amplifier. The action of going to "read" triggers the 0.5 second timer which controls contacts $K_{1a}$ and $K_{1b}$. Contact $K_{1a}$ shorts input No. 2 of final amplifier for the first 0.5 sec. Contact $K_{1b}$ connects the input of the integrator to the output of the final amplifier; as a result, input No. 3 of the final amplifier will gradually increase until it is equal to input No. 1. (Remember input No. 2 is still zero.) The digital meter will, therefore, go to a reading of 000.0. At the end of the 0.5 second period, $K_{1b}$ and $K_{1a}$ will open. The value at input No. 3 will be held and will correspond to the antibody blank value since the antibody blank potentiometer is also connected. Since input No. 1 is also the serum blank value, the meter how displays a negative antibody blank value.

M. Insert tube containing the antigen/antibody immunochemical complex in the read station and press COMPUTE. The minimum point detector is first reset to zero. Then it examines the value of the variable gain photometer and stores the minimum point which is fed to input No. 1 of final amplifier. This value corresponds to the antigen/antibody immunochemical complex concentration plus the serum and the antibody blank. Since pins 2 and 3 contain the previously obtained values of antibody and serum blanks, respectively, the value obtained at the meter is the immunochemical complex concentration.

N. Record reading of METER. This is the only number the technician records.

A prototype or preferred embodiment of the invention has recently been built. This is shown in FIGS. 8, 9A and 9B.

Figure 8:
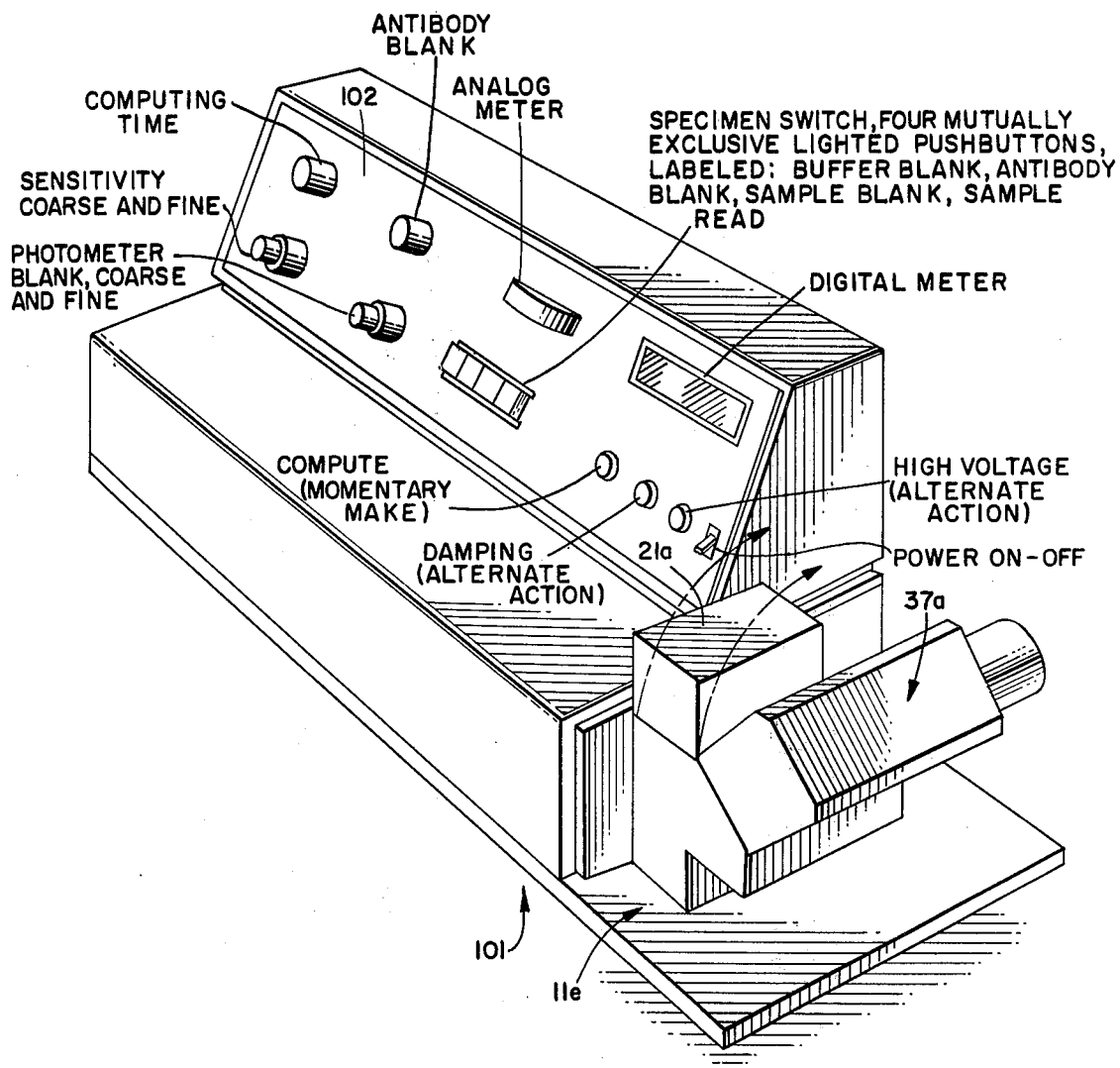
FIG. 8 is a perspective view of a preferred embodiment of the nephelometer, showing the front panel controls and displays and showing the optical testing station.

FIG. 8 shows, in perspective, the external view of the instrument. On the left side is the electrical console 101 and on the right is the optical unit 11e. The latter has a cover 21a which is hinged at the rear edge, unlike the flanged cover 21 of the embodiment of FIG. 1. A hinged cover is obviously more convenient, as it can merely be swung up, back and out of the way on its hinges, as shown by the two dotted lines of FIG. 8, and does not have to be manually removed. The photomultiplier unit, with its high voltage connector projecting to the rear, is at 37a.

The console 101 has a control panel 102 with a number of controls. These controls are labeled, in the Figure, with their designations, so as to correspond with the designations in FIG. 7, and with the designations in the Protocol which was given previously.

Figure 9A:
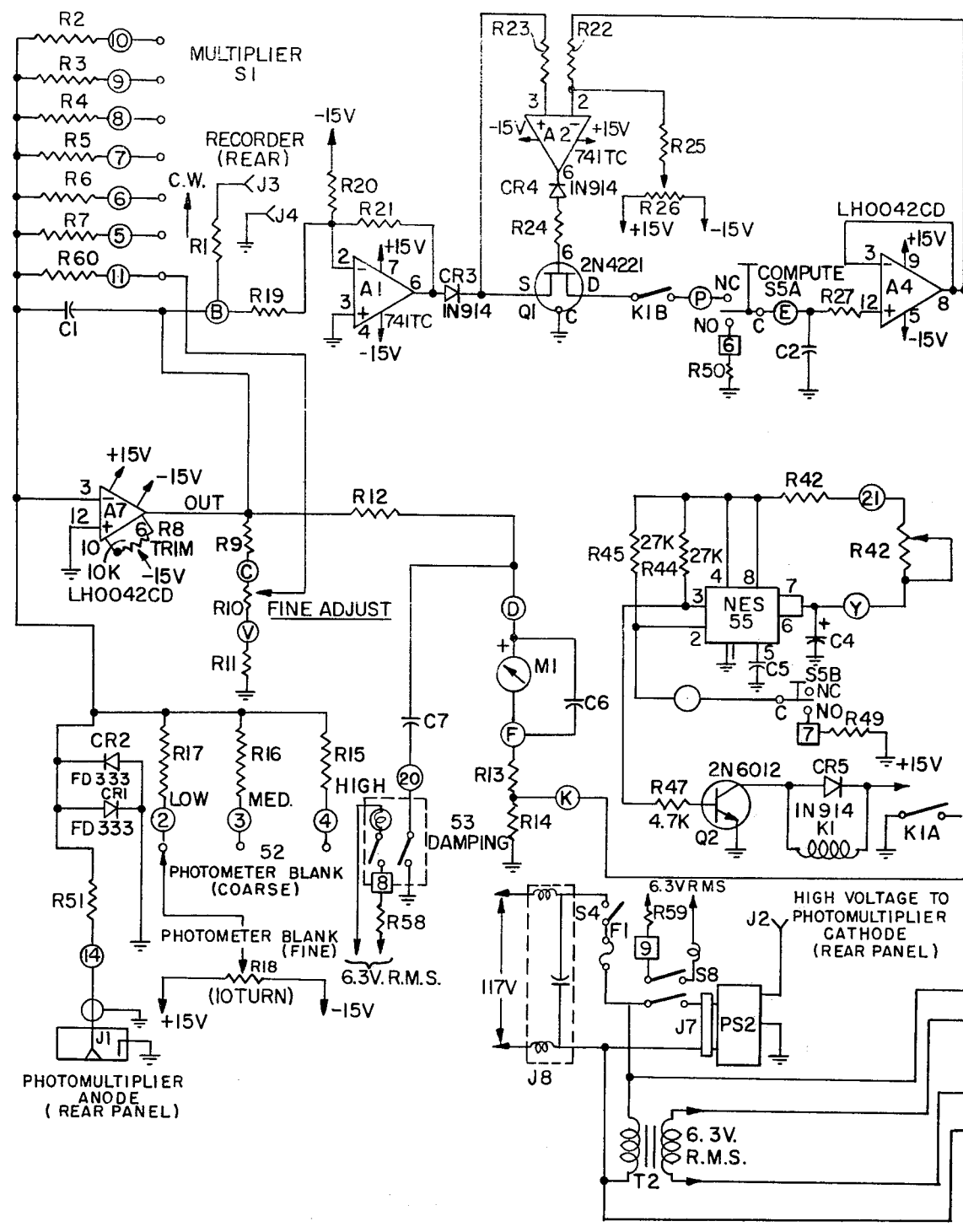
FIGS. 9A and 9B are a schematic of the circuit used in the nephelometer of FIG. 8.
Figure 9B:
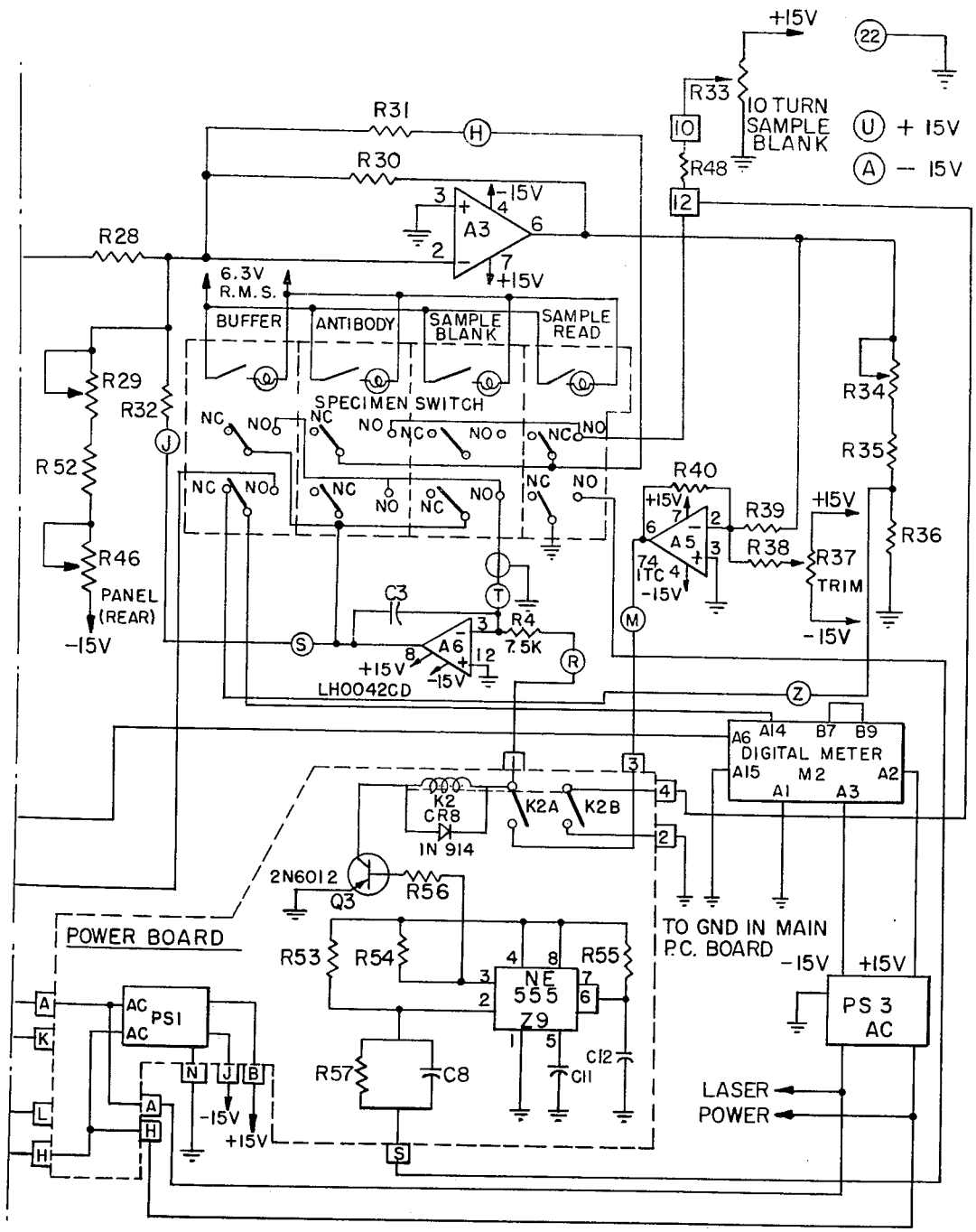

FIGS. 9A and 9B show the wiring diagram in greater detail than in FIG. 7. It will be noted that each of the four SPECIMEN SELECT push buttons and the DAMPING push buttons are self lighting when actuated, thus assisting the operator to keep track of his operations. All of the electronic circuitry is straightforward and uses common components and its action will be self-evident in the light of the previous explanations to the person skilled in the art.

While specific embodiments of an improved method and apparatus have been disclosed in the foregoing description, it will be understood that various modifications within the spirit of the invention may occur to those skilled in the art. Therefore it is intended that no limitations be placed on the invention except as defined by the scope of the appended claims.

I claim:

1. A method of discriminating against the effects of artifacts in optical testing wherein a light beam is directed through material containing particles of interest and wherein such particles are detected by the response of a photosensitive electrical detector located in a selected scatter beam path leading from said material which generates a signal wave containing fluctuating artifact peaks representing fluctuating particles larger than those of interest along with a steady normal signal component representing the particles of interest, comprising inverting said signal wave, adding a constant signal of the same original polarity as said artifact peaks to the inverted signal wave but greater in amplitude than that of the maximum artifact peak, whereby to obtain an inverted signal wave wherein the former artifact peaks are reversed in sense, switching out the reversed artifact peaks of the inverted signal wave, and generating a resultant smoothed output signal from the remainder of the inverted signal wave, whereby the amplitude of said smoothed output signal represents quantitatively the particles of interest unaffected by the fluctuating artifacts from particles larger than those of interest.

2. The method of claim 1, and wherein the switching out of said reversed artifact peaks is performed by comparing said output signal with the inverted signal wave and interrupting said inverted signal wave when its amplitude falls below that of the output signal.

3. In an optical particle measuring system, a transparent container for material containing particles of interest, means to direct a probe light beam through said container, photodetector means in a scatter beam path leading from said container and intersecting said probe light beam, said photodetector means including means to generate a signal wave responsive to the reception of light scattered by said particles of interest along said scatter beam path, said signal wave including peaks caused by fluctuating artifacts larger than the particles of interest along with a steady normal signal component representing the particles of interest, means to invert said signal wave, means to add a constant signal to the inverted wave of the same polarity as but greater in amplitude than the maximum artifact peak, whereby to obtain an inverted signal wave wherein the former artifact peaks form reversed peak portions, means to switch out said reversed peak portions, and means to generate a smoothed output signal from the remainder of the inverted signal wave, the amplitude of said smoothed output signal quantitatively representing the particles of interest without the artifacts.

4. The optical particle measuring system of claim 3, and wherein the means to switch out said reversed peak portions comprises a switch connected between the inverting and adding means and the smoothed output signal generating means, and means to open said switch when the amplitude of the smoothed output signal exceeds the instantaneous amplitude of said inverted signal wave.

5. The optical particle measuring system of claim 4, and wherein said switch-opening means comprises a comparator drivingly connected to said switch, circuit means connecting said smoothed output signal-generating means to one comparison input of the comparator, and circuit means connecting the output of the inverting and adding means to the other comparison input of the comparator.

* * * * *